United States Patent
Strafford et al.

(10) Patent No.: US 7,289,200 B1
(45) Date of Patent: Oct. 30, 2007

(54) CONFOCAL REFLECTOMMETER/ELLIPSOMETER TO INSPECT LOW-TEMPERATURE FUSION SEALS

(75) Inventors: David N. Strafford, Pittsford, NY (US); Michael L. Melocchi, Rochester, NY (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 121 days.

(21) Appl. No.: 11/243,348

(22) Filed: Oct. 4, 2005

(51) Int. Cl.
*G01N 21/00* (2006.01)

(52) U.S. Cl. .................. 356/237.1; 356/237.2

(58) Field of Classification Search ...... None
See application file for complete search history.

(56) References Cited

U.S. PATENT DOCUMENTS

2002/0102749 A1   8/2002   Fielden et al.
2002/0106848 A1   8/2002   Wack et al.
2002/0180985 A1   12/2002  Wack et al.
2005/0012939 A1*  1/2005   Snyder et al. .............. 356/632

OTHER PUBLICATIONS

E. Hecht, Optics (Addison-Wesley, Reading, 1987), pp. 363-368.

* cited by examiner

*Primary Examiner*—Michael P. Stafira
(74) *Attorney, Agent, or Firm*—RatnerPrestia

(57) ABSTRACT

A device and method for measuring a fusion seal quality within a structure comprising a source for providing a focused optical beam of a known intensity to a fusion seal within a structure, the fusion seal reflecting the optical beam according to the fusion seal quality, a receiver for receiving the reflected optical beam and a processor are presented for measuring a intensity ratio between the reflected optical beam and the focused optical beam relating to fusion seal quality. The device may scan the structure and provide an intensity ratio image map for a region within the structure related to fusion seal quality.

20 Claims, 7 Drawing Sheets

CONFOCAL REFLECTOMMETER/ELLIPSOMETER TO INSPECT LOW-TEMPERATURE FUSION SEALS

FIELD OF THE INVENTION

The present invention relates generally to inspecting mirrors blanks and, more specifically, to a quantitative measurement of fusion seal quality within a mirror blank.

BACKGROUND OF THE INVENTION

Mirror blanks may be used for various apparatus including telescopes. Typically a mirror blank includes at least one optical surface. The optical surface may be planar, spherically or aspherically shaped, dependent upon its desired use. The optical surface is typically polished and coated with a reflective coating to provide a mirror.

As mirror blanks become larger, such as those used for space telescopes where their diameters can be greater than 1 m, their design and manufacture become more complex. Mirror blanks may be formed using multiple polygonal shaped glass plates configured to maintain the overall mirror shape. Another design involves the use of a monolithic glass plate with a supporting core structure. In all designs, it is desirable to provide a lightweight mirror blank, so that the supporting structure is designed to be a lightweight core sealed against the glass plate.

For either design, the quality of seals between the core and the plate are typically tested to determine if they are adequately sealed. A flaw in a seal may be defined as an air gap between the core structure and the plate. The quality of the seals in these mirror blanks is typically confirmed by visual inspection and by destructively testing a portion of the mirror blank to find unacceptable flaws.

While many flaws may be detected by visible inspection alone, smaller flaws may go undetected. The visual inspection process may produce a qualitative analysis. However, the inspection is subjective in that a significant flaw determined by one inspector may be determined to be a minor flaw by another inspector. Also, the detection of the same flaw by visual inspection alone may not be repeatable. As the mirror blanks become larger or subject to applications requiring more stringent quality control, the flaw size, depth and concentration of multiple flaws may become more important. Thus, there is a need to develop a quantitative measure to measure mirror blank seal quality.

SUMMARY OF THE INVENTION

The present invention is embodied in a device for measuring a fusion seal quality within a structure, the device including a laser for providing an optical beam and a beam splitter for separating the beam into first and second beams, a first lens for converging the first beam to a focused spot located where a fusion seal is adapted to be located, so that the first beam is reflected by the fusion seal. The device further includes a first detector for detecting an intensity of the reflected first beam and converting the reflected beam into a first electrical signal, a second detector for detecting the intensity of the second beam and converting the second beam into a second electrical signal. The device further includes a processor for determining a ratio between the first electrical signal and the second electrical signal.

The present invention is also embodied in a device for measuring a fusion seal quality within a structure, the device including a source for providing a focused optical beam having a known intensity to a focused spot on a fusion seal within a first surface of the structure so that the focused optical beam is reflected according to a fusion seal quality. The device further includes a receiver for receiving the reflected optical beam and measuring an intensity of the reflected optical beam and a processor for determining an intensity ratio between the received reflected optical beam and the focused optical beam.

The present invention is further embodied in a method for inspecting a fusion seal quality within a mirror blank, the method including the steps of providing an optical beam and separating the optical beam into a first optical beam and a second optical beam, measuring an intensity of the second optical beam, directing and focusing the first optical beam to a fusion seal within the mirror blank and reflecting the first optical beam from the fusion seal, the first optical beam reflected according to a fusion seal quality of the fusion seal. The method further includes the steps of detecting and measuring an intensity of the reflected optical beam and computing an intensity ratio between the intensity of the reflected optical beam and the intensity of the second optical beam.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 1b is a cross section illustration of a portion of the conventional mirror blank shown in FIG. 1a taken along the line B-B of FIG. 1a;

DETAILED DESCRIPTION OF THE INVENTION

Figure 1A:
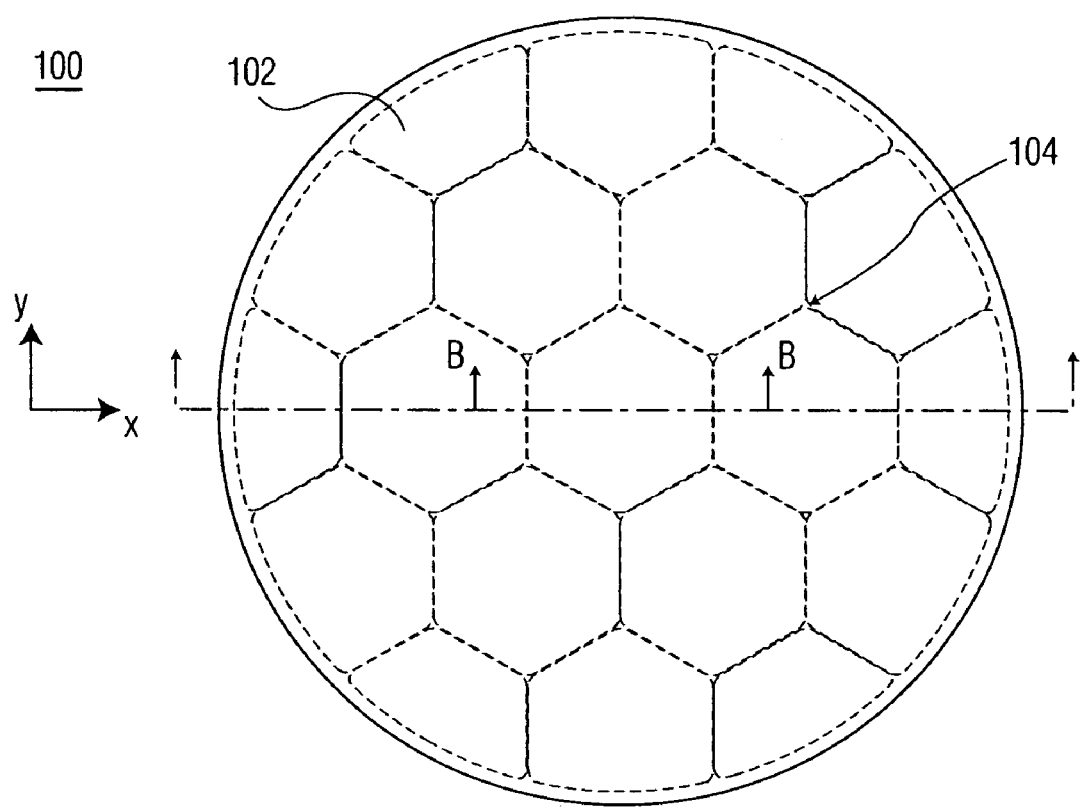
FIG. 1a is an overhead illustration of a conventional mirror blank.
Figure 1B:
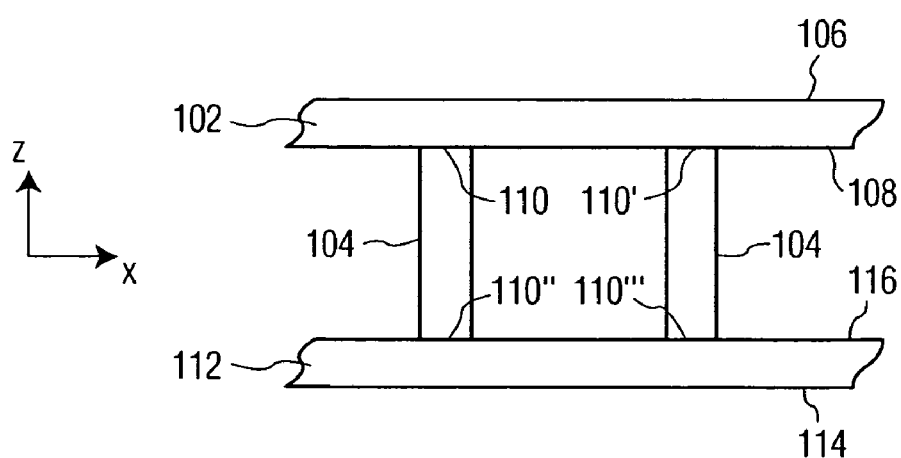

Mirror blanks according to the present invention may be represented by the conventional mirror, as illustrated by FIGS. 1a and 1b. Referring to FIG. 1a, a translucent face sheet 102 is joined to a lightweight translucent honeycomb core 104. Typically, the face sheet may be fused to the core to provide a translucent interface between the face sheet 102 and core 104. Note that face sheet 102 and honeycomb core 104 are not required to be translucent in the visible spectrum. Translucent as described herein refers to being translucent to an optical beam.

Referring now to FIG. 1b, fusion seals within a cross section portion B-B of the mirror blank are shown. Face sheet 102 has an outer surface 106 and an inner surface 108 and this inner surface is joined to core 104 to form fusion seals 110 and 110'. Each fusion seal may have a different seal quality between inner surface 108 and core 104 and are thus represented by 110 and 110'.

Additionally, a second face sheet 112 having an outer surface 114 and an inner surface 116 may be fused to core 104 at inner surface 116. Fusion seals 110" and 110''' result at the core 104 and inner surface 116. The fusion seal quality of fusion seals 110, 110', 110" and 110''' may each vary due to the joining process and may include air bubbles, other air gaps or flaws between a surface 108 or 116 and core 104. A flaw in a fusion seal may have a lateral size (along X and Y directions) as well as a thickness along the Z direction.

Face sheets 102 and 112 and core 104 may be composed of any translucent material that may be transparent to a laser source. Face sheets 102 and 112 and core 104 are desirably composed of material such as ultra low expansion titanium silicate glass, fused silica, $SiO_2$ glass, substantially zero thermal expansion glass ceramic or any other suitable material.

Fusion seal 110 desirably results from the joining of the face sheet 102 with core 104 such that there is a continuity in the translucence at fusion seal 110. Low temperature fusion, frit fusion or other known methods may be used to fuse face sheet 102 to core 104. The fusion seal desirably maintains a glass-glass interface such that light (not shown) directed through fusion seal 110 may be transmitted through the fusion seal with substantially no reflection.

The present invention may be used to measure fusion seal quality on mirror blanks having face plates that are planar, concave spheres, convex spheres or aspherically shaped. For aspheres, the region of curvature may be greater than 1 m. The outer surface 106 of face sheet 102 may be polished or unpolished. The outer surface 114 of face sheet 112 may also be polished or unpolished. Polishing inner surfaces 100, 116 may provide a better seal than if the inner surfaces remain unpolished.

An exemplary system 200 that quantitatively measures a fusion seal quality is now described. A laser source is desirably directed to a fusion seal on the mirror blank. The laser is reflected from the fusion seal according to the quality of that fusion seal. The transmitted and reflected light may be used to determine a quantitative fusion seal quality that is related to a gap thickness between the face sheet 102 and the core 104.

Figure 2:
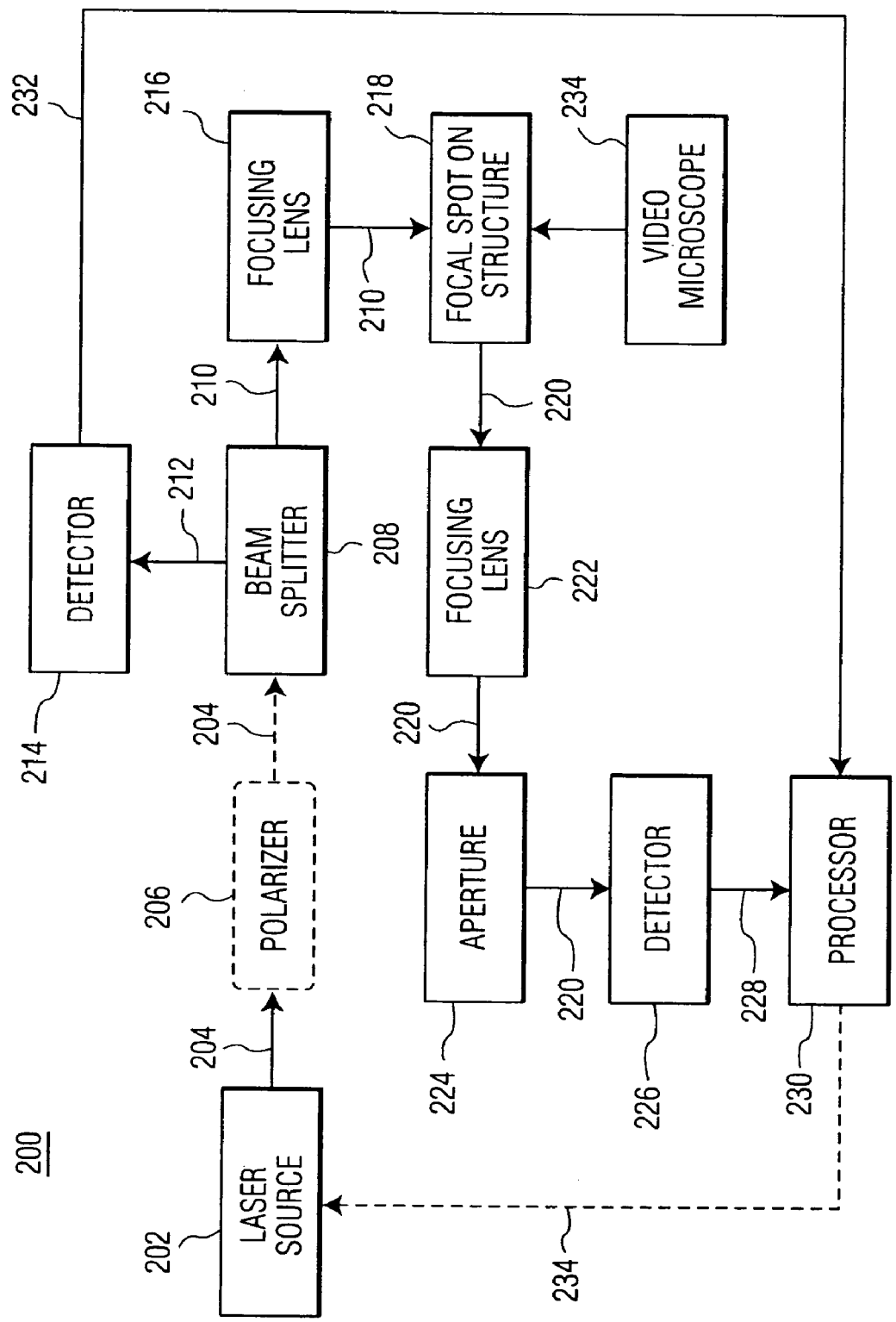
FIG. 2 is a system block diagram of an exemplary fusion seal measurement system of the present invention.

As shown in FIG. 2, exemplary system 200 includes laser source 202 that provides an optical beam 204 to a beam splitter 208. Beam splitter 208 separates the optical beam 204 into optical beams 210 and 212. A polarizer 206 may optionally be used to polarize optical beam 204.

Optical beam 210 is directed to a focusing lens 216 that focuses optical beam 210 onto a focal spot 218 on a fusion seal. An optical beam 220 is reflected from the focal spot 218 with an intensity dependent upon the fusion seal quality. A focusing lens 222 focuses optical beam 220 onto an aperture 224 that filters optical beam 220 to provide filtered optical beam 220 to a detector 226.

Detector 226 detects an intensity of filtered optical beam 220 and converts the optical beam 220 to an electrical signal 228 (circuitry not shown). A detector 214 similarly detects an intensity of optical beam 212 and converts optical beam 212 to an electrical signal 232 (circuitry not shown). Detectors 214 and 226 thus provide intensities of the source and the light reflected according to a fusion seal quality.

Electrical signals 228 and 232 are provided to processor 230. Processor 230 desirably provides a measurement of the fusion seal quality using a normalized ratio of the received reflected intensity to the source intensity. Alternatively, processor 230 may drive the laser modulation, as shown by dashed line 234 between processor 230 and laser source 202. Processor 230 may thus act as a lock-in amplifier to retrieve the detector signals and reject unmodulated background radiation, thereby improving the signal-to-noise ratio.

Laser source 202 provides an optical beam and is desirably a laser diode. A wavelength of the optical beam may depend on the material of the face sheet and core. For example, an optical beam in the infrared spectrum may be used with face sheets and core composed of germanium or zinc selinide. In an exemplary embodiment laser source 202 may be a 10 mW laser diode of 635 nm wavelength producing a 1-mm diameter collimated optical beam.

According to an exemplary embodiment of the present invention, polarizer 206 may desirably provide S-polarized light The polarizer provides for a maximum amount of light to reach the focal spot 210. However, the present invention may be practiced without polarizer 206.

Beam splitter 212 and focusing lens 216 and 222 are known in the art of optical components. In an exemplary embodiment, focusing lens 216 and 222 may each be a 127 mm F/2.8 lens. Other lens that provide focusing may be used within the scope of the present invention.

Aperture 224 may provide a reduction in an amount of flare and scattered light from reflected optical beam 220. In an exemplary embodiment of the present invention, the aperture has a 100 micron diameter. According to an exemplary embodiment of the present invention, aperture 224 desirably has a diameter that is approximately twice the $1/e^2$ optical beam diameter at the surface of a face sheet proximate to the fusion seal. For example, for face sheet 102 of FIG. 1b, the $1/e^2$ optical beam diameter is measured from surface 108 of face sheet 102 that is proximate to core 104. The $1/e^2$ optical beam diameter is known in the art of Gaussian beam optics, from the relationship shown in equation 1, $$2w_0 = \left(\frac{4\lambda}{\pi}\right)\left(\frac{F}{D}\right) \quad (1)$$

where $w_0$ is the $1/e^2$ optical beam diameter at the surface of face sheet, F is the focal length of focusing lens 222, D is the optical beam diameter at focusing lens 222 and $\lambda$ is the wavelength of the coherent light source.

Detectors 214 and 226 are photocurrent detectors and are well known in the art. According to an exemplary embodiment of the present invention, detectors 214 and 226 may be silicon detectors having about a 400-1100 nm range. It is contemplated that any detector that may measure an equivalent optical intensity over at least 6 orders of magnitudes of photocurrent may be used within the scope of the invention.

Processor 230 may be a computer and it may be a portable computer or a workstation computer. Processor 230 may include a digital signal processing (DSP) board with analog-to-digital (A/D) and digital-to-analog (D/A) components. Processor 230 may desirably include software to measure a normalized intensity ratio from electrical signals 228 and 232. Processor 230 may further include a graphical user interface for providing fusion seal quality results in a user interactive manner.

Exemplary system 200 of the present invention may desirably include a video microscope 234 for providing alignment of the optical beam 210 onto focal spot 218. In an exemplary embodiment, a video microscope with a 10× zoom may be used to measure the focal spot size. Maximal positioning of the optical beam desirably results in a minimal focal spot size.

Figure 3:
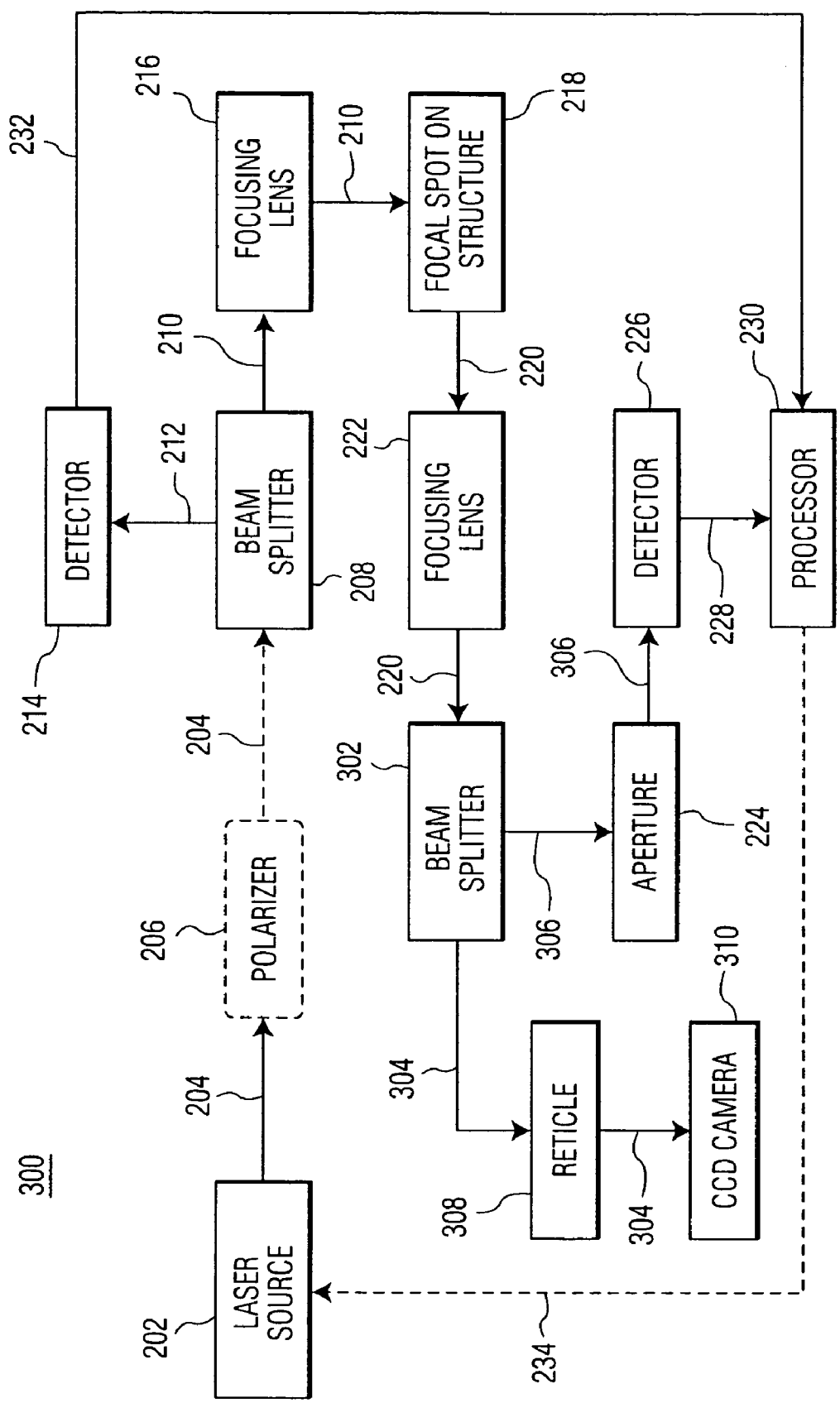
FIG. 3 is a system block diagram of an alternate exemplary fusion seal measurement system of the present invention.

Referring now to FIG. 3, an alternative embodiment 300 of the system diagram of the present invention is now described. Elements that are the same as in the first exemplary embodiment are accorded the same element numbers. As shown in FIG. 3, laser source 202 provides an optical beam 204 to beam splitter 208 that directs an optical beam 210 through a focusing lens 216 to focal spot 218 at the fusion seal. A reflected optical beam 220 reflected according to the fusion seal quality is focused through focusing lens 222. A polarizer 206 may optionally be used to provide a polarized optical beam 204 to beam splitter 208.

In this exemplary system 300, the reflected optical beam 220 is used for alignment rather than video microscope 234 of exemplary system 200. A beam splitter 302 separates reflected optical beam 220 into optical beam 304 and 306. Optical beam 304 is directed to a reticle 308 and a charge-coupled device (CCD) camera 310.

Optical beam 306 passes through aperture 224. Aperture 224 provides a filtered reflected optical beam 306 which is directed to detector 226 that determines an intensity related to the fusion seal quality, as discussed above. Detector 226 provides electrical signal 228 to processor 230. Processor 230 also receives electrical signal 232 from detector 214 which measures an intensity of the optical beam 212 as discussed above. Alternatively, processor 230 may also drive the laser modulation of laser source 202, shown by dashed line 234 between processor 230 and laser source 202, as described above.

In alternative exemplary embodiment system 300 of the present invention, the CCD camera 310 views a portion 304 of reflected optical beam 220. Using the CCD camera 310 for viewing the portion 304 of reflected optical beam 220 may reduce error in an axial conjugate position of detector 226.

As in first exemplary embodiment system 200 of the present invention, processor 230 desirably provides a normalized intensity ratio related to the fusion seal quality as described above.

Reticle 308, beam splitter 302 and CCD camera 310 are known in the art components. Although alternative exemplary embodiment 300 uses a CCD camera, it is contemplated that any optical or electro-optical components may be provided to view optical beam 304 for aligning the system to the focal spot 218.

Figure 4:
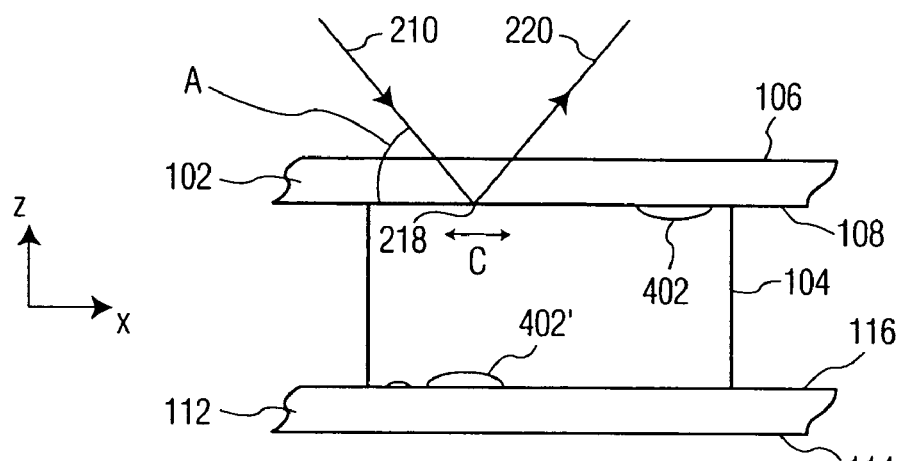
FIG. 4 is a schematic illustration of an exemplary relationship between an incident laser source on a fusion seal of the present invention.

FIG. 4 illustrates a relationship between an incident optical beam and a fusion seal. Referring to FIG. 4, a single portion of a core 104 is shown fused between face sheets 102 and 112 at their respective surfaces of 108 and 116. An optical beam 210 is incident on a focal spot 218 within an XY portion of a fusion seal. The optical beam is incident at an incidence angle A. A reflected optical beam 220 that is a function of the fusion seal quality is reflected from focal spot 218.

Incident optical beam is desirably focused at surface 108 of face sheet 102. Focal spot 218 is desirably scanned across the fusion seal along an X direction indicated by arrows C and along Y direction (not shown). Thus, as focal spot 218 is scanned, it will reflect an optical beam 220 as a function of the glass-fusion seal interface relationship.

When the core 104 is well fused to the surface 108 of face sheet 102, a glass-glass interface will exist. This condition represents a high quality fusion seal. For this condition, a majority of the light that is directed to focal spot 218 will pass through the interface without reflection, thus providing a low intensity of reflected light 220 to be detected.

If a gap in the seal exists, as shown at 402, the intensity of the reflected optical beam 220 increases as a function of air gap thickness between surface 108 and the bottom of gap 402. In this condition, a glass-air interface is formed. Internal reflections of the incident optical beam 210 in the gap 402 will increase, thus providing for an increase in the reflected optical beam 220 and there will be a large change in a normalized intensity ratio in the vicinity of the gap 402.

Similarly, a fusion seal quality may be determined from the fusion seal along surface 116 of face sheet 112. Although not shown, optical beam 210 may be directed at an incidence angle (not shown) to a focal spot on face sheet surface 116 to determine a fusion seal quality along X and Y directions. Thus, a fusion seal gap 402' may be quantifiably identified along surface 116 of face sheet 112 without repositioning the mirror blank.

It is desirable that incidence angle A be provided relative to the XY plane from above a mirror blank. Incidence angle A is about 45° according to an exemplary embodiment of the present invention, but any incidence angle, including normal incidence, may be used. As the incidence angle increases, the reflectance will increase and there may be greater astigmatism and focus errors induced. One skilled in the art may use an increased incidence angle and compensate for the astigmatism and focus errors by utilizing different optical components.

Figure 5:
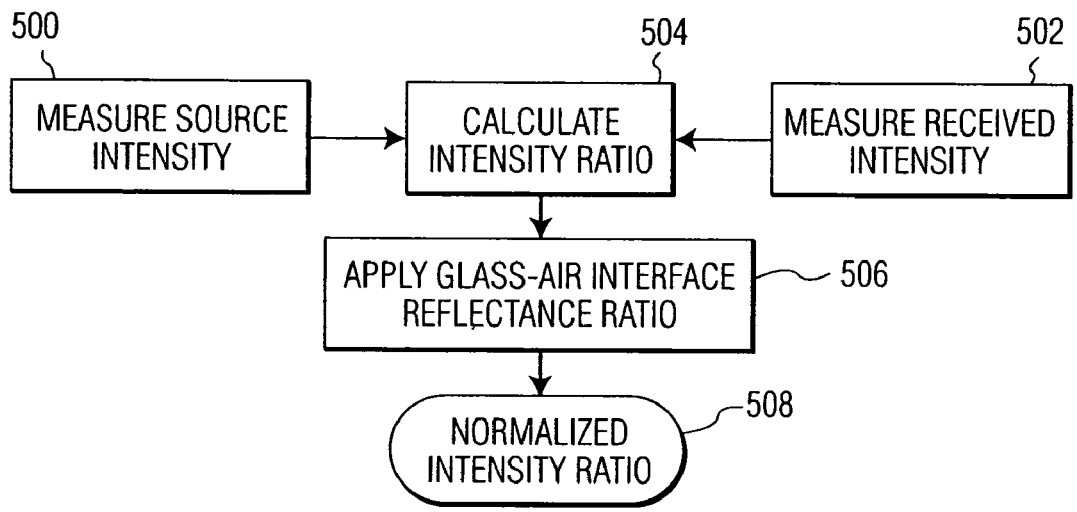
FIG. 5 is a flow chart illustrating an exemplary method of measuring a normalized intensity ratio according to an exemplary embodiment of the present invention.

Referring now to FIG. 5, an exemplary method of measuring a normalized intensity ratio according to an exemplary embodiment of the present invention will be described. In a first step 500, the source intensity is measured as described above. In a second step 502, the filtered received intensity from the fusion seal is measured as described above. Although Steps 500 and 502 are shown separately, it is desirable that they be performed simultaneously.

In a third step 504, the intensity ratio of the received intensity to the source intensity is calculated. In a fourth step 506, an experimentally measured glass-air interface reflectance ratio is applied to the Step 504 intensity ratio. In a fifth step 508, the normalized intensity ratio is provided where the intensity ratio of step 504 is normalized by the glass-air reflectance ratio of step 506. The normalized intensity ratio thus provides an unsealed area of a fusion seal with a greater numerical value than the value provided at a sealed area.

Once a normalized intensity ratio is computed the normalized intensity ratio may be compared to a corresponding gap thickness. The relationship between reflectance ratio and gap thickness may be derived from multiple beam interference relationships.

An air gap of refractive index $n_0$ and thickness d is bounded by a semi-infinite medium of refractive index $n_1$ represented by two glass face sheets. If coherent light of wavelength $\lambda$ is incident on the air gap at an angle $\theta_1$ in medium $n_1$, the total reflected intensity $R_s$ may be given by $$R_S(\lambda, n_0, n_1, d) = \left| \frac{r_S(1 - e^{i\beta_S})}{1 - r_S^2 e^{i\beta_S}} \right|^2 \quad (2)$$

where $$r_S = \left( \frac{n_1 \cos\theta_1 - n_0 \sqrt{1 - (n_1/n_0)^2 \sin^2\theta_1}}{n_1 \cos\theta_1 + n_0 \sqrt{1 - (n_1/n_0)^2 \sin^2\theta_1}} \right) \quad (3)$$

and $$\beta_S = \frac{4\pi}{\lambda} n_0 d \sqrt{1 - (n_1/n_0)^2 \sin^2\theta}. \quad (4)$$

For the present invention, the air gap has a refractive index $n_0$ of 1 and is sandwiched between two glass face sheets of refractive index $n_1$ of 1.5. Given the wavelength of the coherent light source, the theoretical relationship between normalized reflected intensity, $R_s/|r_s|^2$ as a function of air gap thickness d may be computed for the mirror blank parameters of the present invention. An example of the normalized reflected intensity as a function of increasing gap distance at a fixed wavelength is shown in FIG. 8d according to a logarithmic scale.

Figure 6:
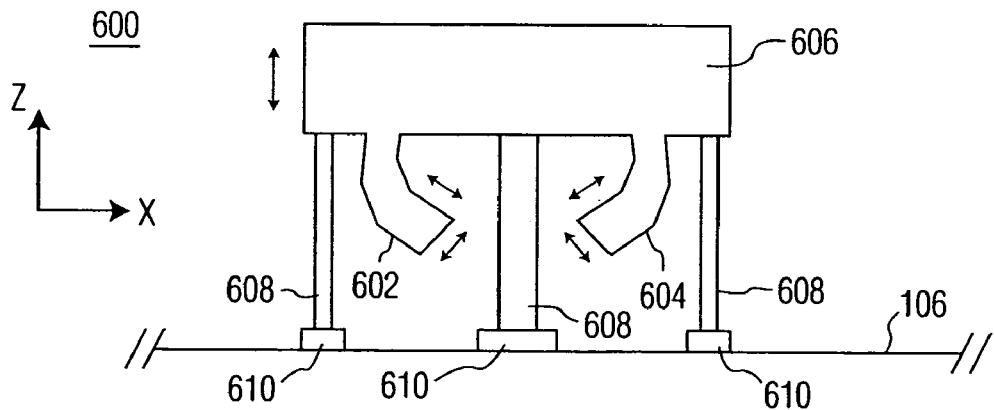
FIG. 6 is an illustration of an exemplary device for performing fusion seal quality measurements of the present invention.

Referring to FIG. 6, an exemplary embodiment of a device for measuring fusion seal quality is described. In this embodiment, a device 600 according to an exemplary embodiment of the present invention is placed on surface 106 of face sheet 102. Device 600 has a source 602 for providing a source optical beam (not shown) that is focused onto a focal spot (not shown) of a fusion seal (not shown). Exemplary device 600 includes a receiver 604 for receiving a reflected optical beam (not shown) from a fusion seal (not shown). Exemplary device also includes a motorized XY translation stage 606 that allows source 602 and receiver 604 to scan across an XY surface of a fusion seal. Exemplary device 600 further includes mounting apparatus 608 with mounting feet 610 to be positioned as desired on surface 106 of a mirror blank. A processor (not shown) desirably computes a normalized intensity ratio according to an exemplary method described above across an XY scan of a fusion seal.

Source 602 of exemplary device 600 desirably includes focusing and source intensity measurement as discussed in exemplary systems 200 and 300 of the present invention. Source 602 desirably includes adjusters to adjust the source position as shown by the arrows.

Receiver 604 of exemplary device 600 desirably includes focusing and filtering through an aperture as discussed in exemplary system embodiments 200 and 300. Receiver 604 desirably includes a received optical beam intensity measurement as discussed above. Receiver 604 desirably includes adjusters to adjust its alignment with the reflected optical beam (not shown).

Motorized XY translation stage 606 allows adjustment of the device lateral (XY) position. Motorized XY translation stage 606 is connected to source 602, receiver 604 and mounting apparatus 608 and provides adjustment of the source 602 and receiver 604 to scan a number of focal spots across an XY plane of a fusion seal. Along with a processor for calculating the normalized intensity ratio as discussed above, the normalized intensity ratio at a number of focal spots provides an XY intensity image map of a fusion seal quality. Depending upon the resolution capabilities of motorized XY translation stage 606, it may be possible to initially resolve a flaw in the intensity image map and then provide a finer-scale resolution to determine details about the flaw.

Device 600 desirably allows measurement across a mirror blank, including fusion seals along the edge of the mirror blank. Device 600 may be repositioned manually to each new fusion seal scan location. Alternatively, device 600 may be automatically positioned to a scan location.

Device 600 desirably has a weight that allows it to be placed onto a mirror. Support feet 610 may include multiple support feet 610 that are each independently adjustable to aid in the alignment of the support feet 610 to structural support locations within the mirror. Device 600 may be portable and allow full mirror blank inspection.

Figure 7:
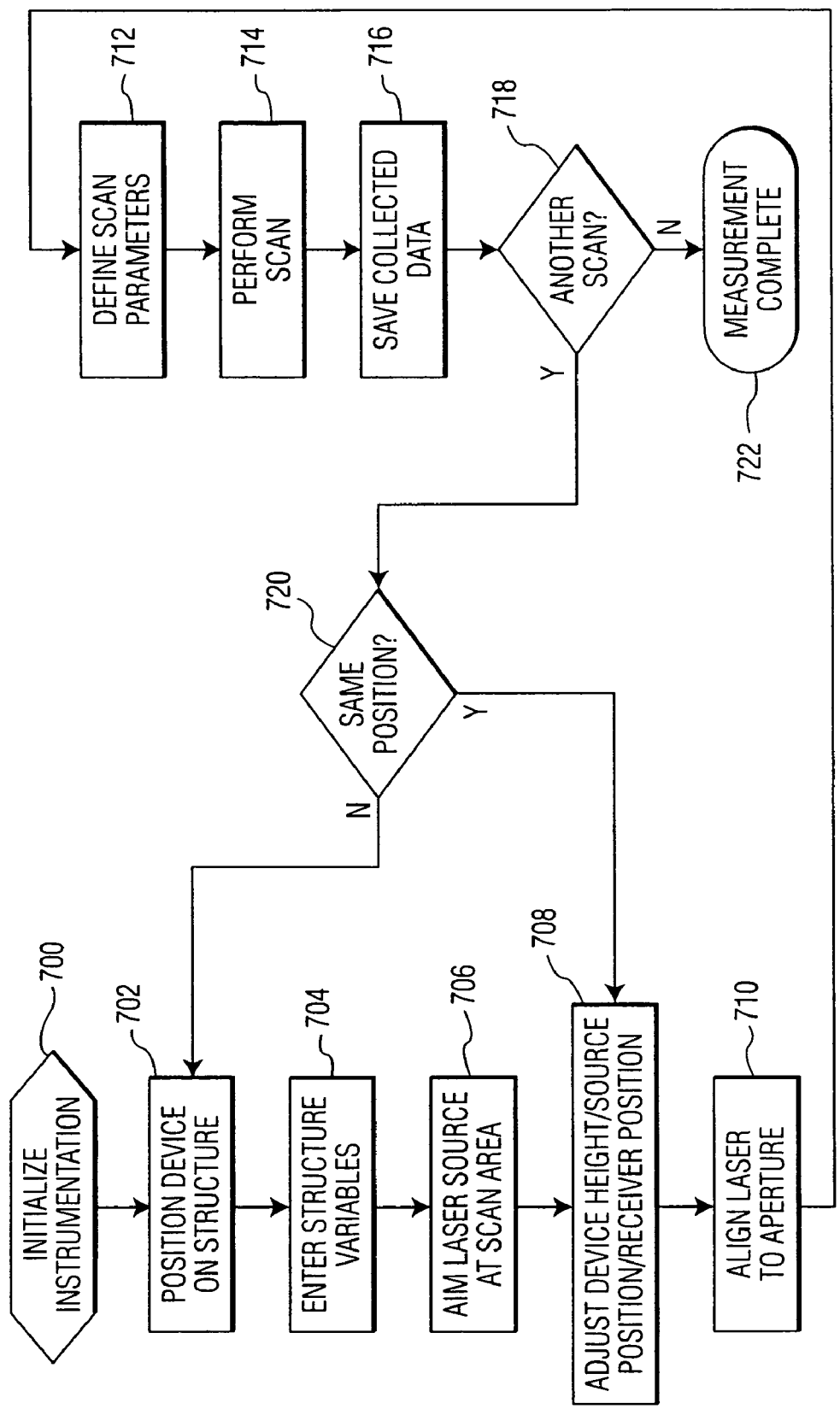
FIG. 7 is a flow chart illustrating an exemplary method of performing a fusion seal quality image map scan according to the exemplary device of the present invention.

Referring now to FIG. 7, an exemplary method of performing a fusion seal quality XY image map scan according to the present invention is described. As shown in step 700, the instrumentation of an exemplary device of the present invention is initialized and as shown in step 702, the device is positioned on mirror blank in a desired location to be scanned. Structure variables may be entered as shown in step 704. These structure variables may include variables such as a face sheet thickness, a face sheet size, a curvature of the face sheet and a polishing factor of the face sheet surface. It is contemplated that other structure variables and other information such as laser source wavelength, laser source power and incidence angle may be included.

A laser source is aimed at a desired scan area, as shown in step 706. The exemplary device may be adjusted for source position, receiver position and/or device height, as shown in step 708. The reflected optical beam from a focal spot is aligned through an aperture as discussed above, as shown in step 710. It should be noted that the order of steps shown in 708 and 710 may be reversed, combined or the step shown in 708 may be repeated after the step shown in 710.

Scanning parameters such as scanning resolution and scanning distance for making a measurement may be provided to the exemplary device, as shown in step 712. Other scanning parameters, such as a dwell time of the source on a focal spot during a measurement, may also be provided within the scope of the present invention. As shown in step 714, the exemplary device performs a scan in the X and Y directions along a fusion seal as desired and data collected during the scan are saved, as shown in step 716. Data desirably includes a normalized intensity ratio image map discussed above over the X, Y coordinates measured according to the scanning parameters.

If a new scan is requested as shown in step 718, the device further determines whether the scan is for a new position or the same position, as shown in step 720. If the scan is for the same position, the method leads to 708 to adjust device source position, receiver position and/or exemplary device height and continues with a scan as discussed above.

If the scan is for a new position, the method returns to 702 and the device is placed in a desired position. A scan continues as described above.

If no other scans are desired, then the method ends with Step 722 and the measurement is complete.

Figure 8A:
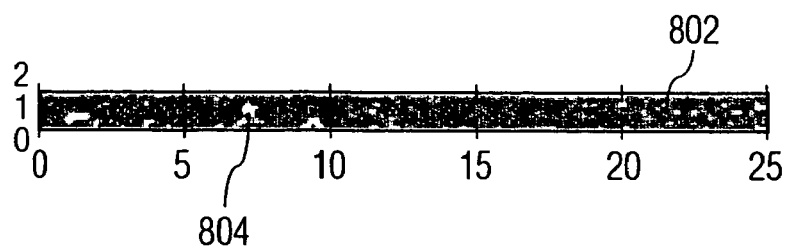
FIG. 8a is an example of a quantitative fusion seal measurement result of the present invention.
Figure 8B:
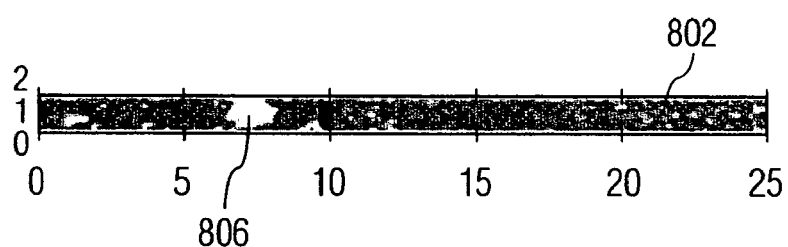
FIG. 8b is another example of a quantitative fusion seal measurement result of the present invention.
Figure 8C:
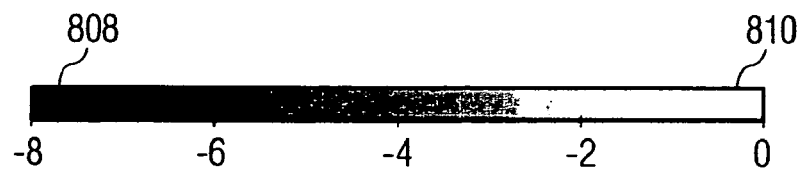
FIG. 8c is an exemplary fusion seal intensity legend for providing a quantitative fusion seal intensity measurement of the present invention.
Figure 8D:
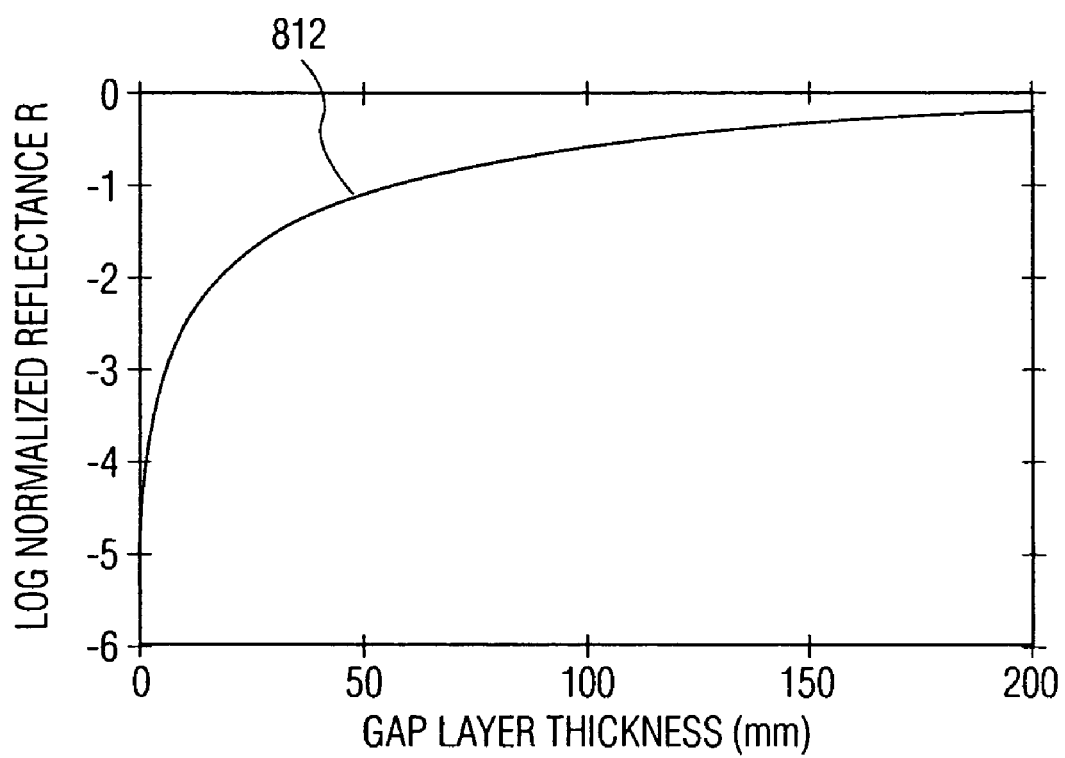
FIG. 8d is an exemplary relationship between an exemplary fusion seal intensity measurement and a gap thickness within a fusion seal of the present invention.

Referring now to FIGS. 8a-d, examples of a normalized intensity ratio scan according to an embodiment of the present invention are described. FIGS. 8a and 8b illustrate two measurement examples of an intensity ratio image map across a typical fusion seal along a 25 mm distance along the X direction and a 2 mm distance along the Y direction. FIG. 8c is an exemplary logarithmic scale intensity legend where the darker the intensity, such as 808 represent a well-fused seal region. Bright areas such as 810 represent a region with a flaw.

FIG. 8a illustrates a fusion seal measurement where a majority of the seal has a high seal quality, i.e. well-fused seal region depicted generally at 802. Only a small flaw 804 is noticeable from the measurement. The location and size of the flaw may be determined from the intensity ratio image map of FIG. 8a. The intensity of the flaw may be further determined by comparing the brightness of flaw 810 to the intensity legend shown in FIG. 8c.

FIG. 8b illustrates a fusion seal measurement where a large lateral flaw 806 is measured. The location and size of the flaw may be quantifiably determined from FIG. 8b, as well as its intensity by comparison to the intensity legend shown in FIG. 8c.

As discussed above, FIG. 8d represents a theoretical normalized intensity ratio $R_s/|r_s|^2$ as a function of gap thickness along the Z axis. The normalized intensity ratio, described above, is presented according to a logarithmic scale. The normalized intensity ratio versus gap thickness further allows a determined flaw to also be quantified in terms of air gap thickness.

Additionally, an intensity image map may be further processed using known in the art methods such as edge detection to produce a database of flaw size, flaw intensity and a number of flaws. This database may be used to aid in manufacture of mirror blanks. As air gap thickness, number and size of flaws tolerances for manufacturing may be determined beforehand, an automated method of fusion seal quality control may be performed.

The present invention may be used to inspect mirror blanks throughout the mirror blank fabrication process, from late stages of grind through final polish. The present invention allows defects in a seal to be detected and corrected during early stages of fabrication. This is desirable, as it may be difficult and costly to attempt to fix a faulty seal at the end of the fabrication process.

An average person with 20/20 vision may typically detect flaws with lateral dimensions as small as 0.1 mm and thicknesses as small as about 40 nm. The present invention may detect similar and smaller lateral dimensions. However, the present invention allows detection of flaws less than 40 nm and has detected thicknesses less than 1 nm.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A device for measuring a fusion seal quality within a structure, the device comprising:
   a laser for providing an optical beam and a beam splitter for separating the beam into first and second beams;
   a first lens for converging the first beam to a focused spot located where a fusion seal is adapted to be located, so that the first beam is reflected by the fusion seal;
   a first detector for detecting an intensity of the reflected first beam and converting the reflected first beam into a first electrical signal;
   a second detector for detecting the intensity of the second beam and converting the second beam into a second electrical signal; and
   a processor for determining a ratio between the first electrical signal and the second electrical signal.

2. The device according to claim 1, the device further comprising at least one of a charge-coupled device (CCD) camera and a video microscope for aligning the reflected first beam to the first detector.

3. The device according to claim 1, the device further comprising:
   a second lens for converging the reflected first beam onto a surface having an aperture for filtering the reflected first beam,
   wherein the filtered reflected first beam is provided to the first detector.

4. The device according to claim 1, the structure further comprising:
   a plate, the plate having a first surface to receive the incident light and a second surface parallel to the first surface; and
   a rib, the rib having a first surface fused, forming a fusion seal, to a portion of the second surface of the plate, the fusion seal receiving the focused spot from the means for converging.

5. The device according to claim 4, wherein the plate and the rib includes materials translucent to the laser.

6. The device according to claim 5, wherein the first surface of the plate is either polished or unpolished.

7. The device according to claim 4, wherein the plate is either piano, concave, convex or aspherical.

8. The device according to claim 4, wherein the aperture has a diameter approximately twice an $1/e^2$ optical beam diameter at the second surface of the plate.

9. The device according to claim 4, wherein the source provides an optical beam at an incidence angle relative to an XY plane and above the first surface of the plate.

10. The device according to claim 9, wherein the incidence angle is about 45 degrees.

11. The device according to claim 1, wherein the processor further normalizes the ratio by a normalization coefficient that is a function of a glass-air interface reflectivity.

12. A device for measuring a fusion seal quality within a structure, the device comprising:
   a source and a beam splitter for providing (a) a focused first optical beam to a focused spot on a fusion seal within a first surface of the structure, so that the focused first optical beam is reflected according to the fusion seal quality and (b) a second optical beam to a detector for detecting an intensity of the second optical beam;
   a receiver for receiving the reflected optical beam and measuring an intensity of the reflected optical beam; and
   a processor for determining an intensity ratio between the received reflected optical beam and the second optical beam.

13. The device according to claim 12, the device further comprising a motorized translation stage coupled to the source and the receiver for positioning the source and the receiver across the first surface of the structure.

14. The device according to claim 13, the device further comprising a mounting apparatus mounted on the first surface of the structure and coupled to the motorized translation stage.

15. The device according to claim 13, wherein the device includes an adjuster to adjust at least one of a source position, a receiver position and a vertical position of the device to provide an optimal position, such that the source and the receiver are confocal.

16. The device according to claim 12, wherein the receiver includes a surface provided with an aperture for filtering at least one of an amount of flare and scattered light from the received reflected optical beam.

17. A method of inspecting a fusion seal quality within a mirror blank, the method comprising the steps of:
   providing an optical beam;
   separating the optical beam into a first optical beam and a second optical beam;
   detecting and measuring an intensity of the optical beam from the second optical beam;
   directing and focusing the first optical beam to a fusion seal within the mirror blank;
   reflecting the first portion of the optical beam from the fusion seal, the optical beam reflected according to a fusion seal quality of the fusion seal;
   detecting and measuring an intensity of the reflected optical beam; and
   computing an intensity ratio between intensity of the reflected optical beam and the intensity of the first optical beam.

18. The method according to claim 17, the method further comprising the step of normalizing the intensity ratio by a normalization constant, such that the normalization constant is a function of a glass-air interface reflectance ratio.

19. The method according to claim 17, the method further comprising the steps of:
   focusing the reflected optical beam and directing the focused reflected optical beam through an aperture in a surface; and
   filtering an amount of flare and scattered light from the focus spot through the aperture.

20. The method according to claim 19, wherein the structure comprises a plurality of fusion seals, the method measuring the fusion seal quality over the plurality of fusion seals, respectively.

* * * * *